(12) United States Patent
Scales et al.

(10) Patent No.: US 12,419,511 B2
(45) Date of Patent: Sep. 23, 2025

(54) PREDICTION OF IOL POWER

(71) Applicant: Johnson & Johnson Surgical Vision, Inc., Irvine, CA (US)

(72) Inventors: Charles Scales, Jacksonville, FL (US); Guang-ming Dai, Fremont, CA (US); Joshua Young, Jacksonville, FL (US); Jeroen Van Der Donckt, Oudenaarde (BE); Michael Rademaker, Ghent (BE); Benjamin Straker, Jacksonville, FL (US); Gilles Vandewiele, Ghent (BE)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 459 days.

(21) Appl. No.: 18/053,342

(22) Filed: Nov. 7, 2022

(65) Prior Publication Data
US 2023/0148859 A1    May 18, 2023

Related U.S. Application Data

(60) Provisional application No. 63/263,940, filed on Nov. 11, 2021.

(51) Int. Cl.
*A61B 3/00* (2006.01)
*A61B 3/10* (2006.01)

(52) U.S. Cl.
CPC .......... *A61B 3/0025* (2013.01); *A61B 3/1005* (2013.01)

(58) Field of Classification Search
CPC .... A61B 3/0025; A61B 3/1005; G16H 20/40; G16H 50/20
See application file for complete search history.

(56) References Cited

U.S. PATENT DOCUMENTS

| | | | |
|---|---|---|---|
| 5,553,156 | A | 9/1996 | Obata et al. |
| 5,819,007 | A | 10/1998 | Elghazzawi |

(Continued)

FOREIGN PATENT DOCUMENTS

| | | |
|---|---|---|
| CN | 110211686 A | 9/2019 |
| DE | 102020101762 A1 | 7/2021 |

(Continued)

OTHER PUBLICATIONS

Berntsen D.A, et al., "Accommodative lag and Juvenile-onset myopia progression in children wearing refractive correction," Vision Research, 2011, vol. 51, pp. 1039-1046.

(Continued)

*Primary Examiner* — Jack Dinh

(57) ABSTRACT

Described are implementations of systems and methods for an improved machine learning-based system that incorporates pre-operative and intraoperative measurements captured during surgery, as well as additional patient-specific data, to provide an individualized, highly accurate post-operative manifest refraction prediction. According to some embodiments, a determination engine generates a predictive feature set of one or more predictors associated with diagnostic measurements of one or more eyes and performs a recursive selection operation using one or more combinations within the predictive feature set and one or more models to produce a most predictive subset, the most predictive subset having a highest prediction accuracy among other predictive subsets for post-operative manifest refraction. The determination engine generates a determination model by refining and retraining the one or more models of the recursive selection operation utilizing the most predictive subset.

6 Claims, 5 Drawing Sheets

(56) References Cited

U.S. PATENT DOCUMENTS

| | | |
|---|---|---|
| 6,400,996 B1 | 6/2002 | Hoffberg et al. |
| 6,513,025 B1 | 1/2003 | Rosen |
| 7,542,947 B2 | 6/2009 | Guyon et al. |
| 8,857,443 B2 | 10/2014 | Hacker et al. |
| 9,560,958 B2 | 2/2017 | Hacker et al. |
| 10,159,406 B2 | 12/2018 | Seesselberg et al. |
| 10,582,847 B2 | 3/2020 | Raymond et al. |
| 10,888,380 B2 | 1/2021 | Bor et al. |
| 11,284,994 B2 | 3/2022 | Huehn et al. |
| 11,382,505 B2 | 7/2022 | Martinez-Enriquez et al. |
| 2018/0296320 A1 | 10/2018 | Gupta et al. |
| 2019/0099262 A1 | 4/2019 | Ladas |
| 2019/0209242 A1 | 7/2019 | Padrick et al. |
| 2020/0015894 A1 | 1/2020 | Bor et al. |
| 2020/0163727 A1 | 5/2020 | Patton |
| 2020/0229870 A1 | 7/2020 | Sarangapani et al. |
| 2020/0350080 A1 | 11/2020 | Elliott et al. |
| 2021/0000542 A1 | 1/2021 | Bor et al. |
| 2021/0106385 A1 | 4/2021 | Bhattacharya et al. |
| 2021/0350936 A1 | 11/2021 | Smith et al. |
| 2021/0369106 A1 | 12/2021 | Campin et al. |
| 2022/0043280 A1 | 2/2022 | Paille et al. |
| 2022/0079433 A1 | 3/2022 | Ladas |
| 2022/0183547 A1 | 6/2022 | Pettit et al. |
| 2022/0189608 A1 | 6/2022 | Pettit et al. |
| 2022/0331092 A1 | 10/2022 | Campin et al. |

FOREIGN PATENT DOCUMENTS

| | | |
|---|---|---|
| EP | 2764854 B1 | 3/2021 |
| EP | 3787473 A2 | 3/2021 |
| EP | 3687450 B1 | 10/2021 |
| EP | 3907701 A1 | 11/2021 |
| WO | 2020012434 A2 | 1/2020 |
| WO | 2020118170 A1 | 6/2020 |
| WO | 2021145815 A1 | 7/2021 |
| WO | 2021148517 A1 | 7/2021 |
| WO | 2021148518 A1 | 7/2021 |

OTHER PUBLICATIONS

Cheng X, et al., "Accommodation and its role in myopia progression and control with soft contact lenses," Ophthalmic and Physiological Optics, 2019, vol. 39, pp. 162-171.

Labhishetty V, et al., "Lags and Leads of Accommodation in Humans: Fact or Fiction?," Journal of Vision, 2021, vol. 21 (3), pp. 1-18.

Mutti D, et al., "Accommodative Lag Before and After the Onset of Myopia," Investigative Ophthalmology & Visual Science, Mar. 2006, vol. 47 (3), pp. 837-846.

Thibos L.N, et al., "Modelling the Impact of Spherical Aberration on Accommodation," Ophthalmic & Physiological Optics, 2013, vol. 33, pp. 482-496.

PREDICTION OF IOL POWER

RELATED APPLICATIONS

This application claims the benefit of and priority to U.S. Provisional Patent Application No. 63/263,940, entitled "Prediction of IOL Power from Structured and Unstructured OCT Data and Electronic Health Records," filed Nov. 11, 2021, the entirety of which is incorporated herein by reference.

FIELD OF INVENTION

The disclosure is related to systems and methods for dioptric prediction of manifest spherical equivalence.

BACKGROUND

In ophthalmology, a patient can have an eye condition that requires a surgery to implant an intraocular lens (IOL), which is an artificial replacement for an original crystalline lens of a patient. Where the IOL physically settles upon implantation is key to a successful surgery, and settlement is used to select an optical power of the IOL selected for a given patient.

A surgeon can utilize conventional calculators to provide lens position estimations that assists in determining the outcome for a patient. Conventional calculators require interoperative data, utilize lens estimations, and perform overt calculations (i.e., calculate final lens position and refractive outcome) to provide these lens position recommendations. However, acquiring and utilizing such interoperative data, estimations, and calculations increases costs and time of the surgery.

SUMMARY

According to an embodiment, a method is provided. The method includes generating, by a determination engine executed by one or more processors, a predictive feature set of one or more predictors associated with diagnostic measurements of one or more eyes. The method also includes performing, by the determination engine, a recursive selection operation using one or more combinations within the predictive feature set and one or more models to produce a most predictive subset, the most predictive subset having a highest prediction accuracy among other predictive subsets for post-operative manifest refraction for training data comprising diagnostic measurements and measured post-operative outcomes being associated with one or more optimal attributes of the diagnostic measurements that provide a prediction with zero or near zero post-operative manifest refraction error. The method also includes generating, by the determination engine, a determination model by refining and retraining the one or more models of the recursive selection operation utilizing the most predictive subset, the determination model accounting for post-operative lens settlement.

In some embodiments, the diagnostic measurements comprise dry data from one or more diagnostic machines, the dry data comprising at least structural anatomy of the one or more eyes or position of an original crystalline lens. In some embodiments, the diagnostic measurements accounts for the post-operative lens settlement absent post-operative lens position calculations. In some embodiments, post-operative lens settlement comprises lateral and axial movement in a z-direction. In some embodiments, the recursive selection operation comprises a recursive linear elimination process. In a further embodiment, the recursive linear elimination process may be performed on a basis of a linear support-vector machine. In some embodiments, the determination model comprises a support-vector machine comprising a radial basis function. In some embodiments, the one or more models comprise a support-vector machine and a linear regression algorithm. In some embodiments, the most predictive subset of the one or more predictors are inputs to the determination model and a remaining set of the one or more predictors are not utilized by the determination model. In some embodiments, a number of the one or more predictors is equal to or greater than 1000, and a number of the most predictive subset of the one or more predictors is equal to or less than 50. In some embodiments, the most predictive subset of the one or more predictors are recursively selected with respect to rates of success and accuracy rankings. In a further embodiment, the determination engine comprises at least one of a mean absolute error, median absolute error, root means square error algorithm, and proportion of eyes within a diopter range to determine the rates of success and accuracy rankings for the one or more predictors.

In some embodiments, the determination engine acquires a dataset comprising the diagnostic measurements corresponding to a plurality of patients, the diagnostic measurements comprising at least one selected lens attribute for each of the plurality of patients. In a further embodiment, the at least one selected lens attribute comprises a lens type or a lens power. In another further embodiment, the dataset comprises health record information from a first source and the diagnostic measurements are acquired from a second source. In a still further embodiment, the dataset comprises doctor diagnosis information across the health record information and the diagnostic measurements.

In some embodiments, the diagnostic measurements comprise pre-operative intraocular lens measurement data, such as measurement data from an optical biometer system; precision measurement data; three dimensional data; and biometry data derived from the three dimensional data. Multiple devices are available on the market to take the pre-operative intraocular lens measurements. Examples of two such devices are the IOL Master system, manufactured by Carl Zeiss AG of Oberkochen, Germany, and the Lenstar LS 900 from Haag-Streit USA, Inc. of Mason, Ohio. In a further embodiment, the precision measurement data comprises pre-lens placement information related to final patient vision comprising the zero or near zero post-operative manifest refraction.

In some embodiments, the near zero post-operative manifest refraction includes a tolerance of about +/−0.5 diopters from 0. In a further embodiment, the near zero post-operative manifest refraction is skewed around a negative half of the tolerance. In some embodiments, the determination model utilizes pre-operative data as an input according to the most predictive subset. In some embodiments, the determination model utilizes one or more outputs of one or more algorithms that use the pre-operative data as the input according to the most predictive subset. In some embodiments, the most predictive subset has a prediction accuracy based on a difference between predicted spherical equivalence and actual spherical equivalence that resulted in zero or near zero. In some embodiments, the most predictive subset has a prediction accuracy within about 0.5 D, about 0.75 D, or about 1.0 D of an absolute error. In some embodiments, the determination engine sets minimum thresholds for prediction accuracy. In some embodiments, generating the predictive feature set comprises generating a plurality of predictive subsets comprising different combinations of predictors. In some embodiments, refining the one or more models of the recursive selection operation comprises performing a linear regression algorithm on a plurality of predictors of the most predictive subset. In some embodiments, the determination model accounts for post-operative outcomes for one or more of a monofocal lens, a multifocal lens, a toric lens, an extended depth-of-focus lens, an adjustable lens, or an accommodative lens.

According to another embodiment, a method is provided. The method includes receiving, by a determination engine executed by one or more processors, a first set of diagnostic measurements of one or more eyes prior to undergoing intraocular lens (IOL) implantation. The method also includes calculating, by the determination engine using the first set of diagnostic measurements, an intermediate prediction of post-operative manifest refraction that accounts for post-operative lens settlement. The method also includes receiving, by the determination engine, a plurality of cornea apex position and curvature measurements of the one or more eyes. The method also includes generating, by the determination engine, a predictive feature subset comprising one or more of the plurality of cornea apex position and curvature measurements, the first set of diagnostic measurements, and the intermediate prediction. The method also includes calculating, by the determination engine using the predictive feature subset, a final prediction of post-operative manifest refraction that accounts for post-operative lens settlement associated with one or more IOL parameters, wherein an IOL associated with the one or more IOL parameters is selected for implantation responsive to the final prediction of post-operative manifest refraction being below a threshold.

In some embodiments, calculating the final prediction comprises performing a linear regression algorithm on the predictive feature subset. In a further embodiment, the predictive feature subset comprises a subset of the one or more of the plurality of cornea apex position and curvature measurements, the first set of diagnostic measurements, and the intermediate prediction having a highest prediction accuracy among other subsets for post-operative lens settlement for training data comprising diagnostic measurements and measured post-operative lens settlement outcomes.

According to one or more embodiments, any of the method embodiments above can be implemented as an apparatus, a system, and/or a computer program product.

According to another embodiment, a system is provided. The system comprises an infrared laser, and a computing sub-system comprising a memory storing a determination engine and a processor executing the determination engine. In embodiments, the determination engine during execution is configured to: receive a first set of diagnostic measurements of one or more eyes prior to undergoing intraocular lens (IOL) implantation; calculate, using the first set of diagnostic measurements, an intermediate prediction of post-operative manifest refraction; receive, via the infrared laser, a plurality of cornea apex position and curvature measurements of the one or more eyes; generate a predictive feature subset comprising one or more of the plurality of cornea apex position and curvature measurements, the first set of diagnostic measurements, and the intermediate prediction; and calculate, using the predictive feature subset, a final prediction of post-operative manifest refraction associated with one or more IOL parameters, wherein an IOL associated with the one or more IOL parameters is selected for implantation responsive to the final prediction of post-operative manifest refraction being zero or near zero.

According to another embodiment, a laser apparatus is provided. The laser apparatus includes an infrared laser; and a computing sub-system comprising a memory storing a determination engine and a processor executing the determination engine. In embodiments, the determination engine during execution is configured to cause the laser apparatus to: generate a predictive feature set of one or more predictors associated with diagnostic measurements of one or more eyes; perform a recursive selection operation using one or more combinations within the predictive feature set and one or more models to produce a most predictive subset, the most predictive subset having a highest prediction accuracy among other predictive subsets for zero or near zero post-operative manifest refraction for training data comprising diagnostic measurements and measured post-operative outcomes; and generate a determination model by refining and retraining the one or more models of the recursive selection operation utilizing the most predictive subset.

According to one or more embodiments, the laser apparatus embodiment above can be implemented as a method, a system, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Figure 1:
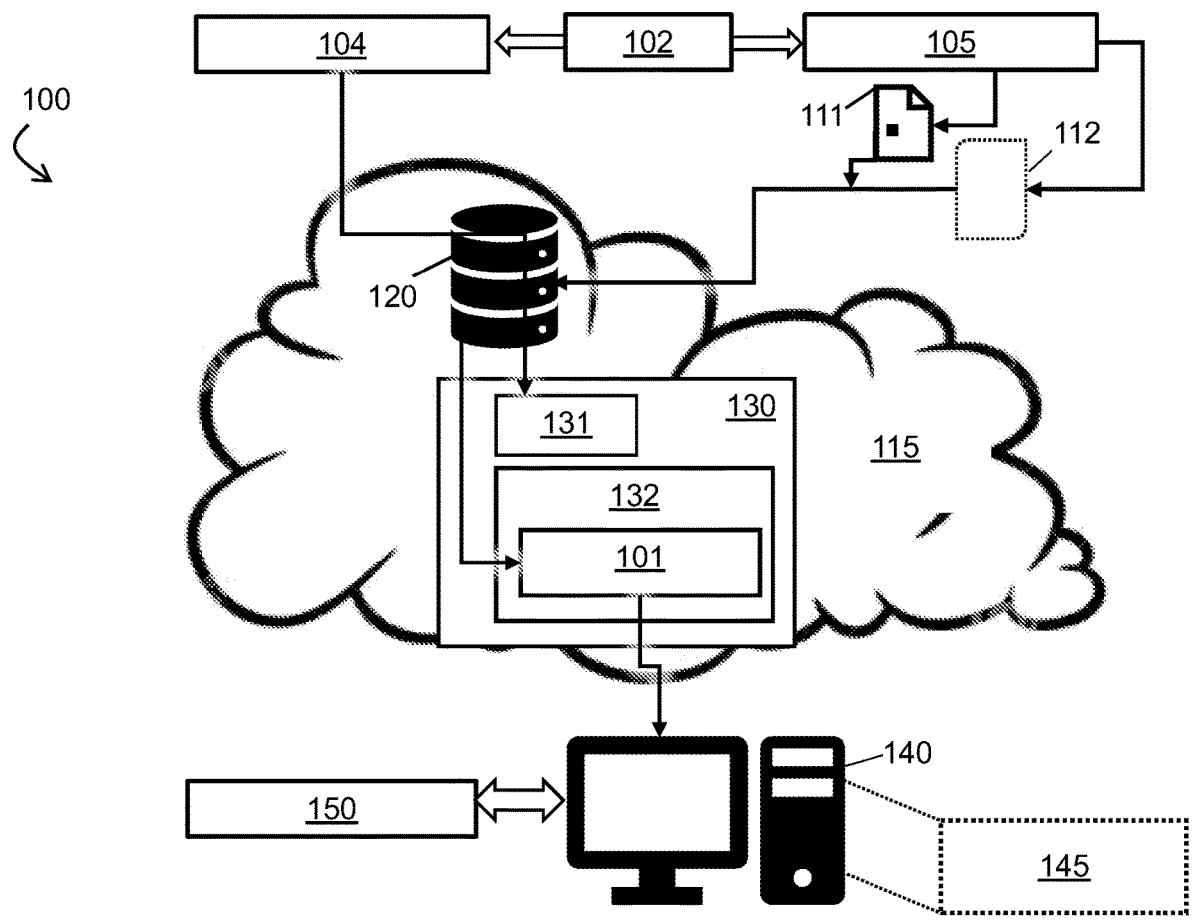
FIG. 1 illustrates a system according to one or more embodiments.

Disclosed herein are systems and methods for accounting for post-operative lens settlement in field of ophthalmology. Generally, in ophthalmology, a surgeon who is performing an implant IOL surgery needs to determine how an implanted IOL will settle over time within a patient's eye. If a surgeon does not consider this settlement, the IOL may not provide optimal refraction, and hence patient vision, as the eye heals.

In implementations of implant IOL surgery not utilizing the systems and methods discussed herein, surgeons may use an algorithm such as the Barrett Universal II formula, created by Graham Barrett in 2010, or the Kane formula, created by Jack Kane in 2017, to predict by how much a manifest refraction will be impacted by post-operative lens position. These formulae utilize pre-surgical measurements including axial length, keratometry, and optical anterior chamber depth (ACD), and the desired post operative refraction. Pre-surgical measurements, sometimes referred to as "dry" measurements, may refer to measurements performed at any time prior to cutting operations (e.g. while a patient is prepped for surgery or during opening stages of a surgical session, prior to performing any incisions or before the patient's eye is impacted by the surgical procedure, as well as during prior diagnostic sessions or physician visits). Accordingly, in some implementations, "pre-surgical" may include measurements taken on the day of the surgery, but prior to any incision or contact with the patient. Different algorithms utilize different base data sets, but are relatively accurate on average across large populations—approximately 75% of the time, post-operative refraction is within about half a diopter (about ±0.5 D) of the algorithm's prediction.

However, these algorithms have two significant impairments. First, the algorithms are based on an underlying data set which is gathered from a specific population (e.g. Caucasian Americans) and may not be applicable to other demographic groups. Second, the algorithms may be statistically accurate on average, but may be inaccurate for any individual patient, with high numbers of patients experiencing more than 1 diopter (≥1.0 D) of change during the healing and settling process. For example, in one experimental study, the Kane and Barrett formulae predictions were accurate to within half a diopter for 76 and 73% of the study population, but also had approximately 5% of the population with greater than 1.0 diopter of shift or settlement.

To address these and other issues, the present disclosure is directed to implementations of an improved machine learning-based system that incorporates pre-operative and intraoperative measurements captured during surgery, as well as additional patient-specific data, to provide an individualized, highly accurate post-operative manifest refraction spherical equivalent prediction. Specifically, before implantation of the new lens, a laser-based surgical system such as the CATALYS™ Precision Laser System from Johnson & Johnson Surgical Vision, Inc. (Irvine, CA) may make thousands of high definition measurements of the patient's eye and cornea. These measurements may be used for accurate placement of laser incisions for removal of the old lens, and may also be utilized as inputs to a machine learning-based determination engine. Accordingly, rather than just relying on average population-wide data, implementations of the systems discussed herein utilize patient-specific measurements gathered during the initial stages of surgery to quickly and accurately predict post-operative manifest refraction that accounts for IOL settlement. In one test, implementations of these systems were able to improve accuracy to 83% for settlement within 0.5 D of prediction, and only approximately 3% of patients had post-operative refraction greater than 1.0 D different from prediction after lens settlement, nearly twice the performance of implementations not utilizing the systems and methods discussed herein (that had post-operative IOL refraction difference greater than 1.0 D for approximately 5% of patients, as discussed above). In addition to accuracy, once trained, the disclosed systems and methods are fast and efficient in operation, with calculations able to be performed in real time or near-real time.

According to one or more embodiments, systems and methods implement artificial intelligence and/or machine learning (ML/AI) operations via a determination engine to process at least pre-operative data in view of post-operative lens settlement concerns. In some implementations, the determination engine may process both pre- and intra-operative data. Pre-operative data may comprise one or more of eye shape measurements including anterior eye and axial length; and electronic health record information including diopter measurements, the presence or absence of glaucoma, patient demographic information, and/or other measurements including blood pressure, antibody presence, past surgical experience, etc. Intra-operative data may comprise one or more of cornea surface measurements including hundreds or thousands of surface position and curvature measurements made to calculate intrastromal fillet paths or placement of other surgical openings. As discussed above, pre-operative or intra-operative data may include pre-surgical measurements or "dry" measurements performed at any time prior to cutting operations (e.g. prior to performing any incisions or before the patient's eye is impacted by the surgical procedure).

According to one or more embodiments, the determination engine intakes and processes a dataset. The dataset, which is further described herein, can include diagnostic data of patient eyes. The dataset can also include thousands of measurements or features that indicate a spherical equivalence of the eye, sometimes referred to as predictors. The dataset may also include electronic health record information, data from diagnostic examinations, patient health history, measurements such as temperature or blood pressure, or any other such data. The dataset may be stored in any suitable format, including as XML data, a string of values in a predetermined order, parameter-value pairs in an array, a flat file, a relational database, or any other such format. From the dataset, the determination engine generates a predictive feature set, some of which can be associated with diagnostic measurements of eyes of patients. In some implementations, the predictive feature set may be referred to as a subset of features, as a set of principal components, or by other similar terms. In parallel, the determination engine performs a recursive selection operation using combinations within the predictive feature set and models to produce a most predictive subset, or a subset of features that have the largest predictive effect on the post-operative refraction error or IOL settlement. For example, out of the thousands of features of the input data set, a subset of 20-30 features may provide the highest accuracy predictions, with additional features having little to no effect on the output prediction. Accordingly, in many implementations, the most predictive subset may be a subset of features that, in combination, have the largest influence on the predictive accuracy relative to other subsets. As discussed above, predictive accuracy may comprise a measure of what percentage of patients have post-operative IOL settlement within a threshold diopter range of a predicted output value, such as within about about 0.3 D, about 0.5 D, about 1.0 D or any other such range. In some implementations, predictive accuracy may also take into account a standard deviation or spread of the prediction, or what percentage of patients have settlements greater than a threshold (e.g. about ±1.0 D), as well as what percentage of patients have settlements within a desired lower threshold (e.g. about ±0.5 D). In many implementations, if a prediction is not perfect (i.e. ±0.0 D), small deviations may be nonetheless acceptable (e.g. about ±0.3 D), and accordingly, a system may be considered highly accurate if a high percentage (e.g. 80%, 90%, 100%, etc.) of patients have settlements within the small deviation range or near to it (e.g. about ±0.5 D). Similarly, in some implementations, a system that has perfect or near perfect predictions for 50% of patients (e.g. about ±0.1 D) may be considered to have lower accuracy if the other 50% of patients have predictions that are off by greater than 1.0 D or more. Accordingly, in different implementations, accuracy may be relative to the entire set of patients or a subset, and may depend both on how close predictions are and how broadly the prediction settlement error is.

According to one or more embodiments, the most predictive subset of the one or more predictors are recursively selected with respect to rates of success and accuracy rankings, including one or more of a mean absolute error, median absolute error, root means square error algorithm, and proportion of eyes within a diopter range to determine the rates of success and accuracy rankings for the one or more predictors. Then, the determination engine generates a determination model by refining and retraining the models utilizing the most predictive subset. Because the most predictive subset is utilized by the determination model, the determination accounts for post-operative lens settlement when providing the prediction. With this prediction from the determination engine, the surgeon can properly select a replacement lens for which post-operative settlement will result in zero or near-zero manifest refraction.

FIG. 1 is a system 100 according to one or more embodiments. The system 100 can generally be viewed as a combination of diagnostic, surgical, user, and medical device equipment. Note that items and elements of the system 100, while shown in the singular, are representative of one or more of that item or element. The system 100 illustrates a determination engine 101 that predicts an IOL will result in zero or near-zero manifest refraction.

The system 100 includes a patient 102 who interacts with a hospital device 104 and a diagnostic device 105 to produce at least a portion of clinical information. Generally, clinical information is any form of data, statistics, measurements, dates, identifiers, and the like from any source. Clinical information can include health record information and/or diagnostic measurements, as well as predictors associated therewith. In one or more embodiments, the clinical information or portions thereof can include the predictors, such as cornea apex position and curvature at anywhere from dozens to thousands of individual points across the cornea surface. For instance, over time, thousands of patients can provide thousands of instances of health record information and diagnostic measurements, some of which include pre-operative and post-operative data. By way of example, the hospital device 104 can create health record information. The health record information can be optionally used by the determination engine 101. Further, the diagnostic device 105 can create diagnostic measurements, such as pre-operative vision parameters, presence or absence of glaucoma, intraocular pressure, blood pressure, etc. Written documentation, referred to generally as documentation 111, and diagnostic measurement data 112 represent the clinical information, such as pre-operative data for templating (by the determination engine 101) the IOL implant from the old crystalline lens and as the diagnostic measurements, or selection IOL parameters. The hospital and diagnostic devices 104 and 105 can communicate to an external system, such as a cloud environment 115. The external system (e.g., the cloud environment 115) can include a data/web service 120. In this way, the data/web service 120 acts as a repository for the clinical information.

The clinical information can be accessed by the determination engine 101, which resides on a device or devices 130. The device 130 can include one or more processors 141 and memory devices 132. For example, device 130 may comprise a server or appliance computing device, a cluster of appliances or servers, a cloud of virtual computing devices executed by one or more physical computing devices, or any other arrangement of a computing device or devices. The determination engine 101 and the device 130 can further communicate with a device 140, with an application 145 thereon, that is utilized by a medical professional 150. In some implementations, device 130 may be referred to a server device, host device, host system, software service, web service, Internet service, or by similar terms, and device 140 may be referred to as a user device, client device, or by similar terms. In turn, the medical professional 150 can interact with the determination engine 101, via the application 145, to select an IOL which will result in zero or near-zero manifest refraction. Application 145 may be a dedicated or custom application for communicating and interacting with the determination engine 101, or may be a web browser or similar application in some implementations. For example, Application 145 may comprise a web browser communicating with a web server provided by device 130 to provide queries to and receive responses from the determination engine 101 (e.g. via an API, remote procedure calls, RESTful requests via HTTP, or any other suitable communication protocol).

The patient 102 can be any person seeking medical treatment and/or care. In this regard, the patient 102 can include any age, gender, health condition, etc. As used in here, by way of example only, the patient 102 is a person who may require replacement of one or both lenses of their eyes, and therefore is seeking advice and possible surgery from a medical professional.

The medical professional 150 can be any person providing medical treatment and/or care. Example of the medical professional 150 include, but are not limited to surgeons, doctors, medical clinicians, medical technicians, medical staff, nurses, and medical assistants.

Generally, the hospital device 104, the diagnostic device 105, and the device 140 can structurally be any computing device comprising software and/or hardware, such as a general-purpose computer, with suitable interface circuits for transmitting and receiving signals to and from other items of the system 100. The device 130 and the data/web service 120 can be similarly any computing device. Each of these devices can include one or more processors (i.e., the processor 131) and one or more memories (i.e., the memory 132). By way of example, the device 130 and the data/web service 120 are shown as virtual and/or distributed devices in the cloud environment 115.

The hospital device 104 can be representative of a hospital or doctor office computer system that aggregates health record information. The diagnostic device 105 can be representative of medical diagnostic equipment (e.g., an auto-analyzer machine), surgical tools, and the like. Examples of the device 140 may be a mobile phone, a smart phone, smartwatch, tablet or other portable smart device, a stationary or standalone computer processor, a desktop or laptop computer, and the like. The device can further include a screen for providing surgical microscope heads-up displays, electronic health records, mobile patient-journey applications, and individual-level provider heads-up displays for the purpose of providing the predictions of the appropriate lens selection to achieve zero or near-zero manifest refraction.

The cloud environment 115 may be a wired network, a wireless network, and/or include one or more wired and wireless networks, such as an intranet, a local area network (LAN), a wide area network (WAN), a metropolitan area network (MAN), a short-range network, a direct connection or series of connections, a cellular telephone network, or any other network or medium capable of facilitating communication between the items of FIG. 1 using any one of various communication standards/protocols (e.g., Bluetooth, Wi-Fi, Zigbee, Z-Wave, near field communications (NFC), Zigbee, infrared (IR), Ethernet, Universal Serial Bus (USB), or any other communication standards/protocols). Additionally, several networks may work alone or in communication with each other to facilitate communication in the cloud environment 115. In some instances, the device 130 and/or the data/web service 120 may be implemented as a single physical server on the cloud environment 115. In other instances, the device 130 and/or the data/web service 120 may be implemented as a virtual server a public cloud computing provider (e.g., Amazon Web Services (AWS®)) of the cloud environment 115.

The data/web service 120 can database (e.g., an SQL database) and/or another storage mechanism. Thus, the data/web service 125 can be used as a repository for storage across the system 100. According to one or more embodiments, the data/web service 120 can store clinical information (as described herein), as well as machine learning models, determination models, driver components, native APIs, and the like for use by the determination engine 101.

The processor 131, in executing the determination engine 101, may be configured to receive, process, and manage the clinical information of the data/web service 120. The processor 131 may be any type of general or specific purpose processor, including, but not limited to, a central processing unit (CPU), application specific integrated circuit (ASIC), field programmable gate array (FPGA), graphics processing unit (GPU), controller, multi-core processing unit, three-dimensional processor, quantum computing device, or any combination thereof. The processor 131 may also have multiple processing cores, and at least some of the cores may be configured to perform specific functions. Multi-parallel processing may also be configured. In addition, at least the processor 131 may be a neuromorphic circuit that includes processing elements that mimic biological neurons. The processor 131 can also be representative of cloud processing across the system 100.

The memory 132 is an example of a (non-transitory) computer readable storage medium, where the determination engine 101 and other software can be located/managed and/or any information (e.g., clinical information communicated from the data/web serve 120) can be stored. For instance, the memory 320 can include, but is not limited to, any combination of a read only memory (ROM), a random-access memory (RAM), internal or external Flash memory, embedded static-RAM (SRAM), solid-state memory, cache, static storage such as a magnetic or optical disk, or any other types of volatile or non-volatile memory. Non-transitory computer readable storage mediums may be any media that can be accessed by the processor 131 and may include volatile media, non-volatile media, or the like. For example, the ROM may be coupled to a system bus and may include a basic input/output system (BIOS), which controls certain basic functions of the device 130, and the RAM is read-write memory coupled to the system bus 215 for use by the processors 310. Non-transitory computer readable storage mediums can include any media that is removable, non-removable, or the like. The memory 132 can also be virtualized and distributed across the cloud environment 115.

Generally, the determination engine 101 utilizes ML/AI algorithms to automatically code, ingest, interpret, and distribute the clinical information from the hospital and diagnostic devices 104 and 105. Note that, while operations and variations of the determination engine 101 are further described herein, the determination engine 101 generally predicts a final surgical outcome for a patient (e.g., in terms of manifest refraction spherical equivalent or spherical and cylindrical power), where the final surgical outcome is a stable manifest refraction (e.g. less than a threshold settlement amount, such as less than about ±1.0 D, about ±0.5 D, about ±0.3 D or any other such value) after healing from lens implantation (e.g., 0-90 days post-operation or up to 6 months).

Figure 2:
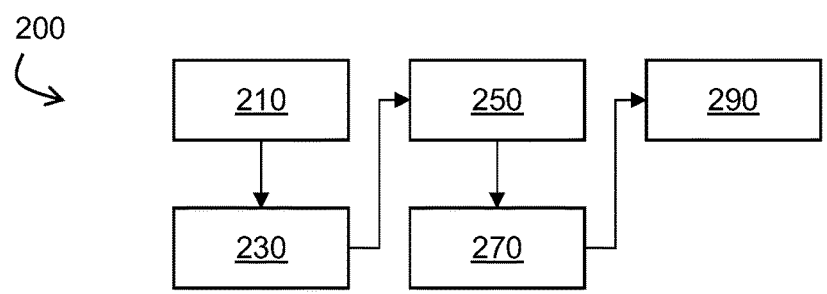
FIG. 2 illustrates a method according to one or more embodiments.

By way of example, turning now to FIG. 2, a method 200 is illustrated according to one or more embodiments. The method 200 can be implemented by the determination engine 101. The method begins at block 210, where the determination engine 101 acquires a dataset including one or more predictors. At block 230, the determination engine 101 processes the dataset to merge data therein across one or more patients. In some implementations, input data may be in unstandardized formats, particularly with electronic health records entered by different organizations or entities (with corresponding different syntaxes, structures, schema, etc.). Accordingly, in some implementations, the input data may be parsed and translated or normalized prior to processing. At block 250, the determination engine 101 generates a predictive feature set from the one or more predictors. At block 270, the determination engine 101 performs a recursive selection operation to determine a most predictive subset. At block 290, the determination engine 101 generates a determination model utilizing the most predictive subset.

According to one or more embodiments, the determination engine 101 can be configured in hardware, software, or a hybrid implementation. For example, determination engine 101 can be stored as software components, modules, engines, instructions, or the like for execution by the processor 131 to cause the device 130 to operate. Note that the determination engine 101 can be viewed as a combination of instructions/software across the system 100, including server instances that communicates with other elements of the system 100 and client instances (i.e., the application 145). For example, the determination engine 101 can have specific software instances that implement particular operations of total engine itself. For instance, the determination engine 101 can include the application 145 that acts as a client software instance. Client software instances can employ one or more of artificial intelligence, modeling, machine learning algorithms, and clinical calculation algorithms that mirror capabilities of the determination engine 101, while offloading processing responsibility.

As noted herein, clinical information is any form of data, statistics, measurements, dates, identifiers, and the like from any source. According to one or more embodiments, the clinical information can include raw patient data instances in varying mediums/forms and can include refined diagnostic information based on the raw patient data instances. Thus, the clinical information contemplates a variety of vision related data, treatments, diagnostic data, and measurements that can be used by the system 100 to determine a vision state and used to correct vision.

According to one or more embodiments, the clinical information (e.g., a dataset including predictors) can include any information for at least vision care, examples of which include derived from the health record information of the hospital device 104 and/or the diagnostic measurement of the diagnostic device 105. For example, the diagnostic device 105 can provide the diagnostic measurements, as itemized herein, as the documentation 111 and/or the data 112. More particularly, the documentation 111 and/or the data 112 can be communicated to and received by at least the device 130 executing the determination engine 130.

The health record information can include, but is not limited to, electronic health records, administrative data, claims data, patient/disease registries, health surveys, and clinical trial data collected during the course of ongoing patient care.

The diagnostic measurements can include, but is not limited to, eye dimension information, ocular characteristics or anatomy, prescription information, eye disease information, eye disease symptoms, cataract information, glaucoma information (e.g., intraocular pressure), dry eye information, surgery system data, and the like. Examples of eye dimension information and/or ocular characteristics or anatomy include, but are not limited to, ocular biometry information, anterior corneal surface information, posterior corneal surface information, anterior lens surface information, posterior lens surface information, lens tilt information, and lens position information. According to one or more embodiments, the diagnostic information includes at least cornea apex position, curvature, intrastromal fillet cuts, and wound placement.

Examples of clinical information (whether the health record information and/or the diagnostic measurement) for at least vision care can also include information regarding custom intraocular lenses, custom contact lenses, custom corneal implants, and the like, which can be configured to treat or ameliorate any of a variety of vision conditions in a particular patient based on their unique ocular characteristics or anatomy.

Examples of clinical information (whether the health record information and/or the diagnostic measurement) for at least vision care can also include, but are not limited to, alternative eye treatment procedure data, spectacle lens information, intraocular lens information, contact lens information, corneal ring implant information, collagenous corneal tissue thermal remodeling information, corneal inlay/onlay information, and corneal implant or graft information, along with parameters related to dioptic power, refractive index, anterior and posterior radius, lens thickness, asphericity, toricity, echelette design, haptic angulation, and lens filter. Further, examples of clinical information (whether the health record information and/or the diagnostic measurement) for at least vision care can include, but are not limited to, various degrees of intraoperative rotation/tip/tilt associated with implantation of an intraocular lens and/or a variety of optical treatment modalities, along with vision treatment shapes or designs that can be administered to a patient.

Figure 3:
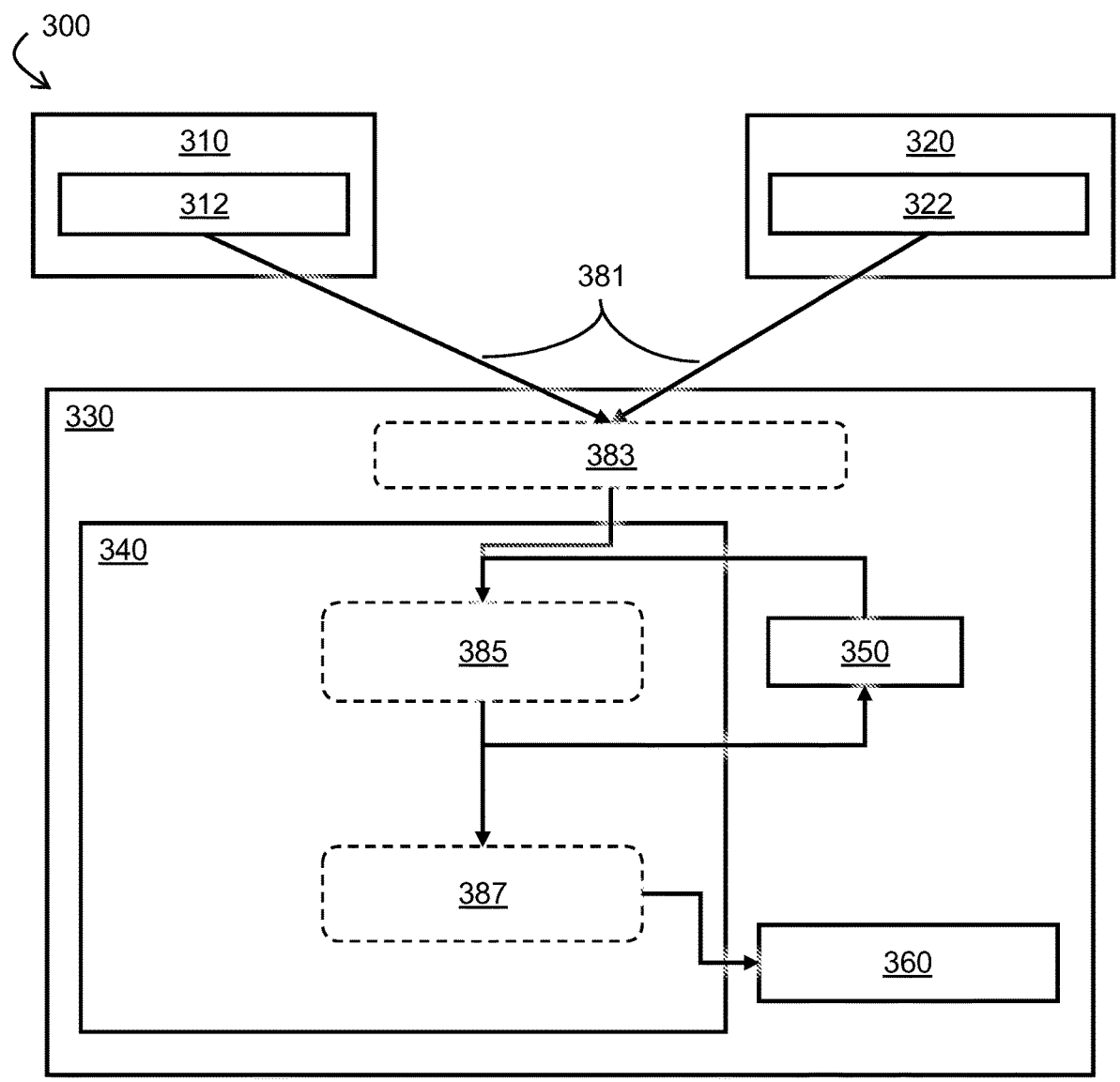
FIG. 3 illustrates a diagram of a determination engine performing operations according to one or more embodiments.

Turning now to FIG. 3, a diagram 300 of the determination engine 101 performing operations according to one or more embodiments is illustrated. The diagram 300 illustrates a first source 310 (e.g., the hospital device 104) storing health record information 312, a second source 320 (e.g., the diagnostic device 105) storing diagnostic measurements 322, and a determination engine 330 (e.g., the determination engine 101) including a ML/AI algorithm 340, as well a model 350 and a determination model 360.

The diagram 300 illustrates the determination engine 330 acquiring a dataset (see arrows 381). Acquiring the data set may comprise receiving the dataset from a client device or another process, e.g. as a query, or acquiring the data set may comprise retrieving the dataset from a memory or storage device, in various implementations. The dataset can optionally include the health record information 312. The dataset can include the diagnostic measurements 322. The dataset can include predictors (e.g., for instance over 2,000 position and/or surface curvature features that indicate or track to a spherical equivalence). The dataset can correspond to a plurality of patients. According to one or more embodiments, the dataset includes at least cornea apex position and curvature. The diagnostic measurements 322 can include at least one selected lens attribute for each of the plurality of patients. The at least one selected lens attribute includes a lens type or a lens power.

According to one or more embodiments, the health record information 312 and the diagnostic measurements 322 can be part of a corpus of clinical information gathered and/or measured across a plurality of patients. For instance, the dataset can include doctor diagnosis information across the health record information 312 and the diagnostic measurements 322.

As noted herein, the health record information 312 can include, but is not limited to, electronic health records, administrative data, claims data, patient/disease registries, health surveys, and clinical trial data collected during the course of ongoing patient care. According to one or more embodiments, the diagnostic measurements 322 can include pre-operative intraocular lens biometric data, precision measurement data (e.g., data from a CATALYS™ Precision Laser System from Johnson & Johnson Surgical Vision, Inc. (Irvine, CA)), three dimensional data associated with structures of the eye, and biometry data derived from the three dimensional data.

The precision measurement data can include pre-lens placement information related to final patient vision comprising the zero or near zero post-operative manifest refraction. The data of the CATALYS™ Precision Laser System include optical coherent tomography (OCT) measurements and 'integral guidance' data. For example, OCT is a three dimensional imagining technique that uses individual A-scans to identify anatomical surfaces of a human eye. Each A-scan acquires surface information for the anterior cornea, posterior cornea, iris, anterior lens, and posterior lens. The OCT performs over 10,000 A-scans to get a high resolution data covering the full volume of the anterior segment. The full volume is constructed from the scanned 3-D surfaces. Independent scans are then completed to provide axial and sagittal cross-sections. The OCT scans can be provided on a display to a surgeon (e.g., the medical professional 145). According to one or more embodiments, OCT measurements of the CATALYS™ Precision Laser System can include 3D mapping of the optical surfaces of most of the anterior segment, i.e., front and back curves of the cornea and front and back curves of the crystalline lens. The different optical surfaces are registered to each other in x-, y-, and z-dimensions. The registered surfaces are examples of the diagnostic measurements 322 used/leveraged/exploited by the determination engine 101.

According to one or more embodiments, the diagnostic measurements 322 can include dry data from one or more diagnostic machines. The dry data can include at least structural anatomy of the one or more eyes or position of an original crystalline lens, with the interoperative data being taken when a patient is docked with a diagnosis machine before surgery (i.e., before a laser or cutting implement has impacted the eye, such as "dry" data). Note that interoperative data is not required by the determination engine 330. According to one or more embodiments, the diagnostic measurements 322 can be used to account for the post-operative lens settlement absent post-operative lens position calculations (e.g., without post-operative lens position calculations). Note that post-operative lens settlement can include lateral and/or axial movement in a z-direction.

The diagram 300 illustrates the determination engine 330 processing the dataset (see dashed-box 383) once it is acquired. In this regard, the determination engine 330 can parse, merge, and/or correlate of the dataset according to the plurality of patients, such that patient information of the health record information 312 and of the diagnostic measurements 322 are matched. Further, during processing, one or more predictors associated with the dataset can be organized or generated into a predictive feature set or a subset of features that are predictive of post-operative manifest refraction. Note that the predictive feature set can be associated with the diagnostic measurements 322 of one or more eyes, thereby detailing structural anatomy before any surgery or operation and allow prediction of likely outcome prior to any surgical steps being performed. According to one or more embodiments, the predictive feature set can include pre-operative data, including health record information and/or diagnostic measurements or other data. According to one or more embodiments, the predictive feature set can include one or more outputs of one or more algorithms that use pre-operative data, as well as pre-operative data itself. For example, in some implementations, a prediction algorithm such as a Barrett Universal II or Kane algorithm may be used in a first stage to create an initial or "intermediate" prediction, with the predicted output (e.g. the intermediate prediction) of the algorithm provided as one of a plurality of inputs to a second stage, which may output a final prediction. Note that a number of the one or more predictors can be equal to or greater than 500, such as 1,000 or 2,000. Further, the predictive feature set can be a number that is equal to or less than 500, such as 10, 25, or 50. According to one or more embodiments, the predictive feature set includes at least cornea apex position, curvature, intrastromal fillet cuts, and wound placement.

Once the dataset is acquired, the diagram 300 illustrates the ML/AI algorithm 340 of the determination engine 330 performing a recursive selection operation (see dashed-box 385). The recursive selection operation, by the determination engine 330, generates and implements predictor combinations within the predictive feature set and uses the model 350 to produce a most predictive subset. For instance, the determination engine 330 and the model 350 automatically determine pertinent features/data from the health record information 312 and the diagnostic measurements 322 and match these pertinent features/data to predictor combinations so that the most predictive subset is found. In some implementations, the predictor combinations or subsets may be generated randomly (e.g. via a random forest algorithm) and compared with each other to identify more predictive features. In some implementations, predictive subsets may be merged and mutated via a genetic algorithm to generate additional subsets which may then be compared to identify fitness (e.g. predictive accuracy). In some implementations, a principal component analysis or other feature extractor may be utilized to identify more predictive features from the data set. Subsets consisting of permutations or combinations of these features may be generated and their prediction accuracy compared. In some implementations, a set number of features may be utilized for each subset, with additional iterations adding further features. For example, in one such implementation, single-feature subsets may first be generated and compared. Once the feature subset with the highest accuracy is identified, its feature may be combined with each other feature in two-feature subsets, which may then be compared. This may proceed until a number of predictive features have been selected and an accuracy does not improve with further iterations beyond a threshold value (e.g. if a 30 feature subset has a greater accuracy than a 29 feature subset, the algorithm may continue to iterate; if a subsequent 31 feature subset does not have greater accuracy, the algorithm may stop and the 30 feature subset utilized).

The model 350 can be representative of one or more machine learning models. According to one or more embodiments, the one or more machine learning models can include one or more of a support-vector machine, a linear regression algorithm, logistic regression algorithm, a neural network, and a nearest neighbor operation. The recursive selection operation can include a recursive linear elimination process of the predictive feature set on a basis of the model 350 (such as on the basis a linear support-vector machine) to produce the most predictive subset. For example, in some implementations, the recursive selection operation can include a linear regression algorithm with ridge regression to compare and select subsets having a lowest error or highest accuracy.

As discussed above, according to one or more embodiments, the most predictive subset of the one or more predictors are recursively selected with respect to rates of success and accuracy rankings. The determination engine 330, and more specifically the ML/AI algorithm 340, can include one or more of a mean absolute error, median absolute error, root means square error algorithm, and proportion of eyes within a diopter range to determine the rates of success and accuracy rankings for the one or more predictors.

The subset having the lowest error rates, highest success rate, and/or highest accuracy ranking, referred to as the most predictive subset, may be used to identify one or more optimal attributes of the diagnostic measurements 322 that provide a prediction with zero or near zero post-operative manifest refraction error. In an example, the attributes may be values for various structural anatomy features that correspond to particular interoperative data. Optimal, in this case, can be considered attributes that provide a best indication (i.e., without actually procuring and/or using interoperative data). For instance, the determination engine 330 may analyze rays from the A-scans of the OCT to trace these rays back to determine an optimal anterior chamber depth (ACD) for the new lens.

According to one or more embodiments, the determination engine 101 derives most predictive features (e.g. features most affecting the accuracy, error rate, or success rates, etc.) from the pre-operative and interoperative biometry of the diagnostic measurements 322. Further, the determination engine 101 utilizes one or more several health record information features to be associated with the diagnostic measurements 322 to filter the dataset based on inclusion and/or exclusion criteria. Thus, as a technical effect and benefit, the determination engine 101 can build the determination model 360 from a reasonable dataset that does not include cases that are highly anomalous (e.g., cases where a lens had to be extracted or there is retinal disease associated).

According to one or more embodiments, the determination engine 330 selects ACD predictors to determine a final refractive outcome and does not require final lens position calculation. Rather, the determination engine 330 calculates final refractive outcomes by using post-operative ACD predictors (i.e., to answer the question of 'what is the post-operative manifest spherical equivalence?'), as well as other predictors.

Thus, the most predictive subset can include one or more attributes, such as locations of the old crystalline lens, that are the most predictive of manifest spherical equivalence. In other words, the determination engine 330 provides a templating process of positions of old crystalline lens to predict post-operative manifest refraction that accounts for settlement of new IOLs. The templating process may comprise identifying IOL parameters (size, weight, dimensions, curvature, etc.) such that after post-operative healing, the IOL will likely result in a zero or near-zero manifest refraction. The number of attributes in the most predictive subset can be equal to or less than 50 in many implementations, such as 5, 8, or 10. This may significantly reduce processing and memory requirements compared to using all of the potential thousands of features, as noted above.

The diagram 300 illustrates the determination engine 330 generating the determination model 360 (see dashed-box 387). For example, the determination engine 330 selects a best performing model 350 and refines and retrains that model 350 utilizing the most predictive subset to generate the determination model 360. For example, the model may be periodically retrained with new training data as it is obtained (e.g. the results of new surgeries and post-operative settling). By using the most predictive subset, the determination engine 330 accounts for post-operative lens settlement.

According to one or more embodiments, the determination model 360 can include a support-vector machine comprising a radial basis function. The extracted features of the predictive subset (or a plurality of subsets, during training and optimization) may be used with the training data to identify highly predictive features. In some implementations, this may be more or less efficient, based on the number of features involved. Accordingly, in some other implementations, the determination model 360 may be based on linear regression and a root means square error algorithm or similar algorithm, and proportion of eyes within a diopter range to determine the rates of success and accuracy rankings for the one or more predictors.

According to one or more embodiments, the most predictive subset can be used as inputs to the determination model 360, while a remaining set of the one or more predictors are not utilized. For example, of the thousand-plus potential predictors discussed above, in many implementations, the determination engine may identify a subset such as 5, 8, 10, 20, 50 or similar numbers of predictors, less than the thousand-plus available in the dataset.

According to one or more embodiments, the determination model 360 utilizes pre-operative data as an input according to the most predictive subset. According to one or more embodiments, the determination model 360 utilizes one or more outputs of one or more algorithms (e.g. Barrett Universal II, Kane, etc.) that use the pre-operative data as the input according to the most predictive subset. Note that the determination model 360 can utilize pre-operative data and dry data (e.g., before a laser or cutting implement has impacted the eye) to make a prediction and can utilize post-operative data to self-refine (e.g. via a recursive supervised learning process). Note also that interoperative data is not required by the determination engine 330: with respect to the determination engine 101, interoperative data does not need to be taken during surgery. Rather, according to one or more embodiments, dry data can be taken when a patient is docked with a diagnosis machine before surgery.

Advantageously, the determination engine 330 can infer interoperative data. In this regard, the determination engine 330 seeks and determines the best predictors that infer a final outcome (i.e., that predicts a final surgical outcome for a patient, where the final surgical outcome is a stable manifest refraction after healing from lens implantation). In turn, the determination engine 330 can select or suggest an IOL by inferring a patient's ideal manifest refraction spherical equivalent or spherical and cylindrical power to reach a zero or near zero refraction.

Figure 4:
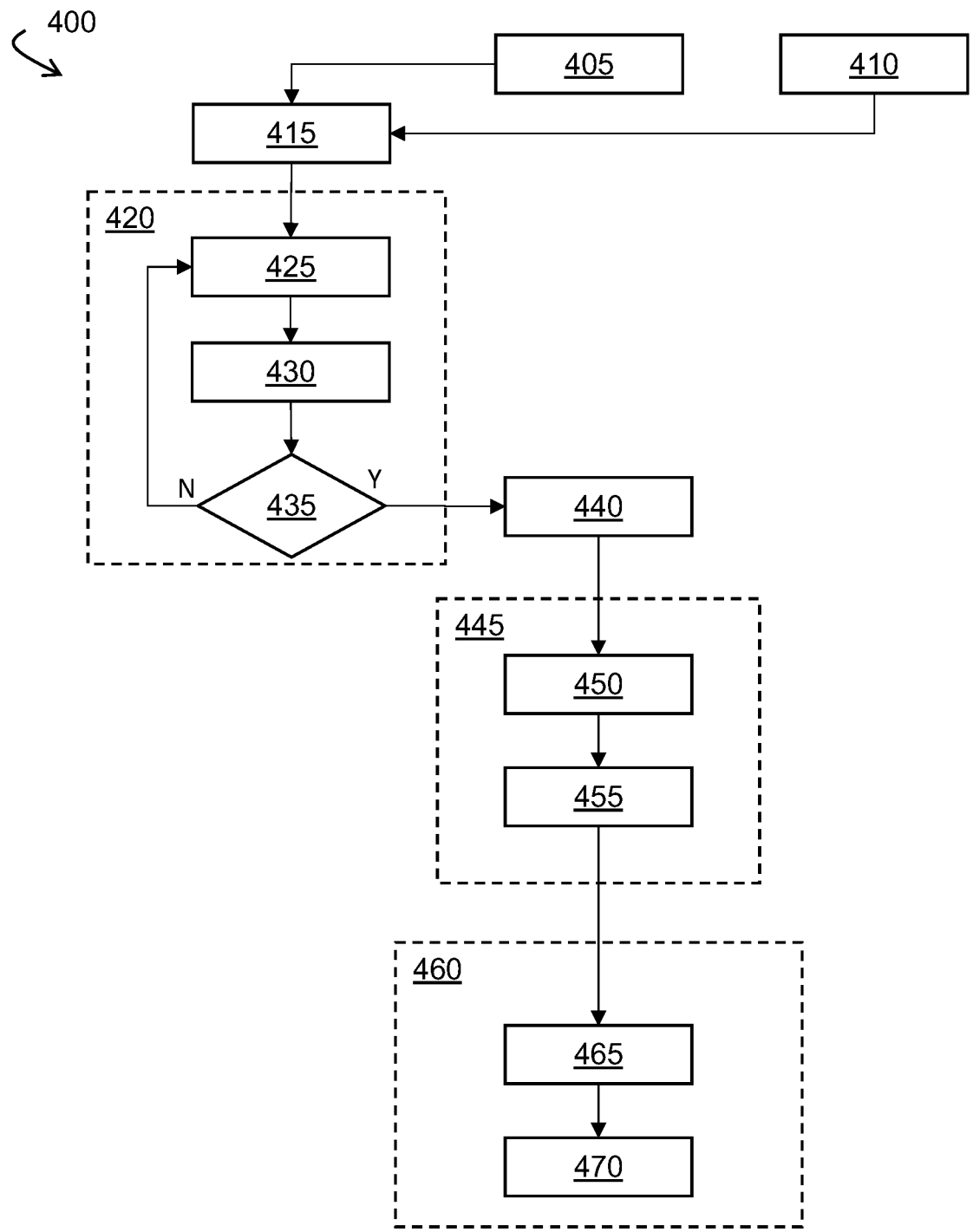
FIG. 4 illustrates a method according to one or more embodiments.

Other operations of the determination engine 101 are contemplated herein. Turning now to FIG. 4, a method 400 is illustrated according to one or more embodiments. The method 400 can be implemented by the determination engine 101. The method begins at block 405, where the determination engine 101 acquires a dataset including one or more predictors. Acquiring the dataset may comprise retrieving the dataset from a memory or storage device responsive to a query or receiving the dataset as part of a query. The dataset may comprise clinical data, patient information including anonymized or aggregated patient information, diagnostic data, and/or values for one or more measurements of attributes.

At block 410, the determination engine 101 acquires outputs from one or more lens settlement calculators. For instance, and by way of example only, the determination engine 101 can acquire outputs of a Barrett Universal II Formula calculator and/or a Kane formula calculator or similar algorithm to assist in refining the determination model. Calculators such as these provide pre-operative lens estimations based on pre-operative diagnostic measurements such as axial length or anterior chamber depth; however, there is room for improvement in their accuracy. Accordingly, implementations of the determination engine described herein can provide an improvement over these calculators through the use of additional measurements before surgery or during initial pre-operative "dry" surgical stages to more accurately predict post-operative refraction.

At block 415, the determination engine 101 processes the dataset and the outputs to merge data therein across one or more patients. As discussed above, merging data may comprise normalizing, rescaling, translating or remapping the data into a format useable by the determination engine (particularly where input data is in different formats). In some implementations, the dataset may be divided into training data and testing or generalization data, which may be useful for avoiding overfilling of a classifier model.

At block 420, the determination engine 101 identifies a most predictive subset of features. In some implementations, this may be done via a recursive subset generation and testing process, iterating until reaching a threshold accuracy or until further iterations do not improve accuracy. In some implementations, at block 425, the determination, generates a predictive feature set from the one or more predictors. As discussed above, in some implementations, subsets of the predictors may be generated, either randomly or iteratively. For example, subsets may be generated via a random forest algorithm in some implementations. In other implementations, subsets may be selected via a plurality of iterations, built up from the previous iteration's most predictive subset until accuracy between iterations does not significantly increase.

At block 430, accuracy of the generated predictive set may be tested. In some implementations, a training data set may be split into subsets for training and testing, or training and generalization. In other implementations, the predictive set may be tested against a randomly selected set of patient data within the training set. Accuracy may be determined in some embodiments by comparing a predicted post-operative refraction for a patient in the training data set to an actual measured post-operative refraction for the patient, with a difference measured in percentages, diopters, or any suitable method. In some embodiments, blocks 425-430 may be performed in series or parallel for a plurality of subsets of features or predictors. For example, in some implementations, each predictor in the set of hundreds or thousands of predictors may be utilized in a single subset in a first iteration; the predictor associated with the highest accuracy may be combined with each other predictor in a plurality of subsets in a second iteration; then the pair of predictors associated with the highest accuracy may be combined with each other predictor in a plurality of subsets in a third iteration; etc. until accuracy reaches a threshold or does not increase between iterations beyond a threshold. In other implementations, combinations of predictors may be selected randomly, via random forest algorithm, or by any other suitable method.

At block 435, the determination engine 101 performs a recursive selection operation to determine a most predictive subset. As discussed above, each subset's prediction accuracy may be tested using the training data and corresponding post-operative outcomes, and the highest accuracy subset selected. In some implementations, this may be done iteratively with the process returning to step 425 after identifying a most predictive subset of the generated subsets in that iteration. For example, a first iteration may involve one feature in each subset, a second iteration may involve two features, etc.; or a first iteration may involve a first random selection of features, a second iteration may be based off a genetic algorithm mutating the highest performing selection from the first iteration, etc. In some implementations, the most predictive subset may be identified responsive to the subset having an accuracy above a threshold. In some implementations, the most predictive subset may be identified responsive to the subset having an accuracy that does not improve more than a threshold amount between iterations. If the accuracy (or accuracy increase) is below the threshold, in some implementations, the recursive selection operation may repeat steps 425-435.

Once a most predictive subset of features is identified, at block 440, the determination engine 101 generates a determination model utilizing the most predictive subset. In some implementations, the calculator outputs (e.g. obtained at block 410) can be utilized to further refine the determination model. For example, the calculator outputs may be used as constraints for one or more variables of the determination model (e.g. such that inputs cannot exceed the calculator outputs), or the calculator outputs may be used as a check on the determination model (e.g. if the model predicts a value different from the calculator output by an amount greater than a threshold, the model may be retrained).

At block 445, in some embodiments, the determination engine 101 generates a first or initial post-operative manifest refraction. In some embodiments, at block 450, this may include receiving or retrieving pre-surgical measurements of one or both eyes of the patient to generate an initial post-operative manifest refraction prediction. The diagnostic measurements may comprise axial length measurements, keratometry, optical anterior chamber depth, or any other suitable data. At block 455, the determination engine may calculate an initial post-operative prediction of final refraction via a pre-operative measurement-based algorithm such as Barrett Universal II or the Kane formula.

At block 460, the determination engine 101 acquires real-time diagnostic measurements (e.g., for the particular patient) and generates a predicted post-operative manifest refraction, sometimes referred to as a final post-operative manifest refraction or outcome. For example, in some embodiments at block 465, the determination engine may receive or retrieve real-time diagnostic measurements determined during initial surgical operations, including cornea apex positions and curvature values at a plurality of positions across the cornea, measured via an infrared laser or other measurement apparatus. In some embodiments, the determination engine may also receive additional data about the patient, including electronic health record information, diagnostic measurements, or other data.

At block 470, the determination engine 101 utilizes the determination model to make a post-operative manifest refraction or outcome prediction. The prediction includes identification or selection of a lens that will provide zero or near zero post-operative manifest refraction error once implanted (and after any settling). The zero or near zero post-operative manifest refraction error includes a difference between predicted spherical equivalence and actual spherical equivalence that resulted in zero or near zero. According to one or more embodiments, a near zero post-operative manifest refraction can include a tolerance of about +/−0.5 diopters from 0 (e.g., the zero or near zero post-operative manifest refraction includes a value at about +/−0.5 D from 0). For instance, the prediction with zero or near zero post-operative manifest refraction error can be within about 0.5 diopters, about 0.75 diopters, and/or about 1.0 diopters of an absolute error. According to one or more embodiments, the near zero post-operative manifest refraction is skewed around a negative half of the tolerance. Thus, in some embodiments, the determination engine 101 can target zero or a slight minus (−0.5<x<0). The determination engine 101 can set minimum thresholds for how often the prediction is zero or near zero.

In some embodiments, a post-surgical follow-up measurement may be performed and the actual post-operative refraction error compared to the prediction. The actual error may be utilized with the predictive values to retrain or update the model (e.g. repeating blocks 420-440).

Figure 5:
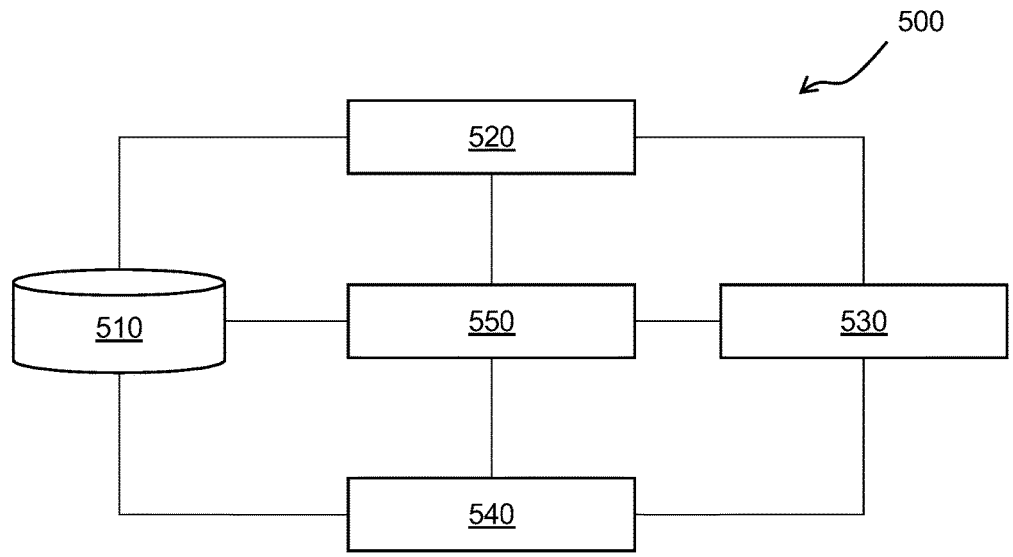
FIG. 5 illustrates an artificial intelligence diagram according to one or more embodiments.

FIG. 5 illustrates an artificial intelligence diagram 500 according to one or more embodiments. The artificial intelligence diagram 500 includes data 510, a machine 520, a model 530, an outcome 540, and (underlying) hardware 550.

The description of FIG. 5 is made with reference to FIGS. 1-4 for ease of understanding where appropriate. For example, the machine 520, the model 530, and the hardware 550 can represent aspects of the determination engine 101 of FIGS. 1-2 (e.g., and the ML/AL algorithm 340 therein), while the hardware 550 can also represent the devices 104, 105, 130, and 140 and/or the data/web service 120 of FIG. 1. In general, the ML/AI algorithms of the artificial intelligence system 400 (e.g., as implemented by the determination engine 101 of FIGS. 1-2) operate with respect to the hardware 550, using the data 510, to train the machine 520, build the model 530, and predict the outcomes 540.

The data 510 can be any data as described herein. For instance, the data can include health record information and diagnostic measurements, as well as doctor diagnosis information across the health record information and the diagnostic measurements. Further, the diagnostic measurements can correspond to a plurality of patients and include at least one selected lens attribute (e.g., a lens type or a lens power) for each of the plurality of patients. The diagnostic measurements can also include pre-operative intraocular lens biometric data such as data from an IOL Master system manufactured by Zeiss AG or any suitable preoperative biometry device, precision measurement data, three-dimensional data, and biometry data derived from the three dimensional data.

The machine 520 operates as the controller or data collection associated with the hardware 550 and/or is associated therewith. The data 510 can be on-going data or output data associated with the hardware 550. The data 510 can also include currently collected data, historical data, or other data from the hardware 550; can include measurements during a surgical procedure and may be associated with an outcome of the surgical procedure; and can be related to the hardware 550. The data 510 can be divided by the machine 520 into one or more subsets.

The machine 520 trains, such as with respect to the hardware 550. This training can also include parsing, analyzing, merging, and correlating of the data 510 collected. In accordance with one or more embodiments, training the machine 520 can include self-training (e.g., a recursive selection operation) by the determination engine 101 utilizing the one or more subsets (e.g., a most predictive subset) For example, the machine 520 can, over a plurality of training operations, recursively use cornea apex position and curvature to calculate intrastromal fillet cuts for primary wound placement.

The model 530 can be an unsupervised learning model, such as a self-discover algorithm, or a supervised learning model, such as a support-vector machine (SVM), that analyze the data 510. For example, a SVM provides a prediction method using a statistical learning framework for classification and regression analysis of the data 510. The model 530 can employ any combination of classification, clustering, regression, anomaly detection, data cleaning, reinforcement learning, structured prediction, feature engineering or learning, semi-supervised learning, decision trees, linear regression, neural or artificial neural networks, logistic regression, recursive selection, relevance vector, and support vector operations, or the like. According to one or more embodiments, the model 530 can be a simplification model that normalizes numbers and formulas utilizing both the SVM and linear regression in conjunction with a learning algorithm architecture. The model 530 can first use the SVM and move toward linear regression operations. The model 530 can clean the data 510 during normalization. As the data 510 is cleaned and the model 415 self-discovers, the model 510 can trend toward white boxing, where internals of the model 530 become stable for viewing (e.g., so the source code can be examined, and weaknesses discovered).

The model 530 (e.g., a machine learning model and/or resulting determination model) is built on the data 510 associated with the hardware 550. Building the model 530 can include physical hardware or software modeling, algorithmic modeling, and/or the like that seeks to represent the data 510 (or subsets thereof) that has been collected and trained. In some aspects, building of the model 530 is part of self-training operations by the machine 520.

The model 530 can be configured to model the operation of hardware 550 and model the data 510 collected from the hardware 550 to predict the outcome 540 (e.g., a prediction with zero or near zero post-operative manifest refraction error) achieved by the hardware 550. Predicting the outcomes 540 (of the model 530 associated with the hardware 550) can utilize a trained model 530. Thus, using the outcome 540 that is predicted, the machine 520, the model 530, and the hardware 550 can be further configured and/or refined, accordingly.

Thus, for the artificial intelligence diagram 500 to operate with respect to the hardware 550, using the data 510, to train the machine 520, build the model 530, and predict the outcomes 540, the ML/AI algorithms therein can include neural networks.

In general, a neural network is a network or circuit of neurons, or in a modern sense, an artificial neural network (ANN), composed of artificial neurons or nodes or cells.

For example, an ANN involves a network of processing elements (artificial neurons) which can exhibit complex global behavior, determined by the connections between the processing elements and element parameters. These connections of the network or circuit of neurons are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1. In most cases, the ANN is an adaptive system that changes its structure based on external or internal information that flows through the network.

In more practical terms, neural networks are non-linear statistical data modeling or decision-making tools that can be used to model complex relationships between inputs and outputs or to find patterns in data. Thus, ANNs may be used for predictive modeling and adaptive control applications, while being trained via a dataset. Note that self-learning resulting from experience can occur within ANNs, which can derive conclusions from a complex and seemingly unrelated set of information. The utility of artificial neural network models lies in the fact that they can be used to infer a function from observations and also to use it. Unsupervised neural networks can also be used to learn representations of the input that capture the salient characteristics of the input distribution, and more recently, deep learning algorithms, which can implicitly learn the distribution function of the observed data. Learning in neural networks is particularly useful in applications where the complexity of the data (e.g., the diagnostic data 322) or task (e.g., monitoring, diagnosing, and treating any number of various diseases) makes the design of such functions by hand impractical.

According to one or more embodiments, the neural network can implement a long short-term memory neural network architecture, a convolutional neural network (CNN) architecture, or other the like. The neural network can be configurable with respect to a number of layers, a number of connections (e.g., encoder/decoder connections), a regularization technique (e.g., dropout); and an optimization feature, as well as building a simplification model discussed herein.

The long short-term memory neural network architecture includes feedback connections and can process single data points (e.g., such as images), along with entire sequences of data (e.g., such as speech or video). A unit of the long short-term memory neural network architecture can be composed of a cell, an input gate, an output gate, and a forget gate, where the cell remembers values over arbitrary time intervals and the gates regulate a flow of information into and out of the cell.

The CNN architecture is a shared-weight architecture with translation invariance characteristics where each neuron in one layer is connected to all neurons in the next layer. The regularization technique of the CNN architecture can take advantage of the hierarchical pattern in data and assemble more complex patterns using smaller and simpler patterns. If the neural network implements the CNN architecture, other configurable aspects of the architecture can include a number of filters at each stage, kernel size, a number of kernels per layer.

Figure 6:
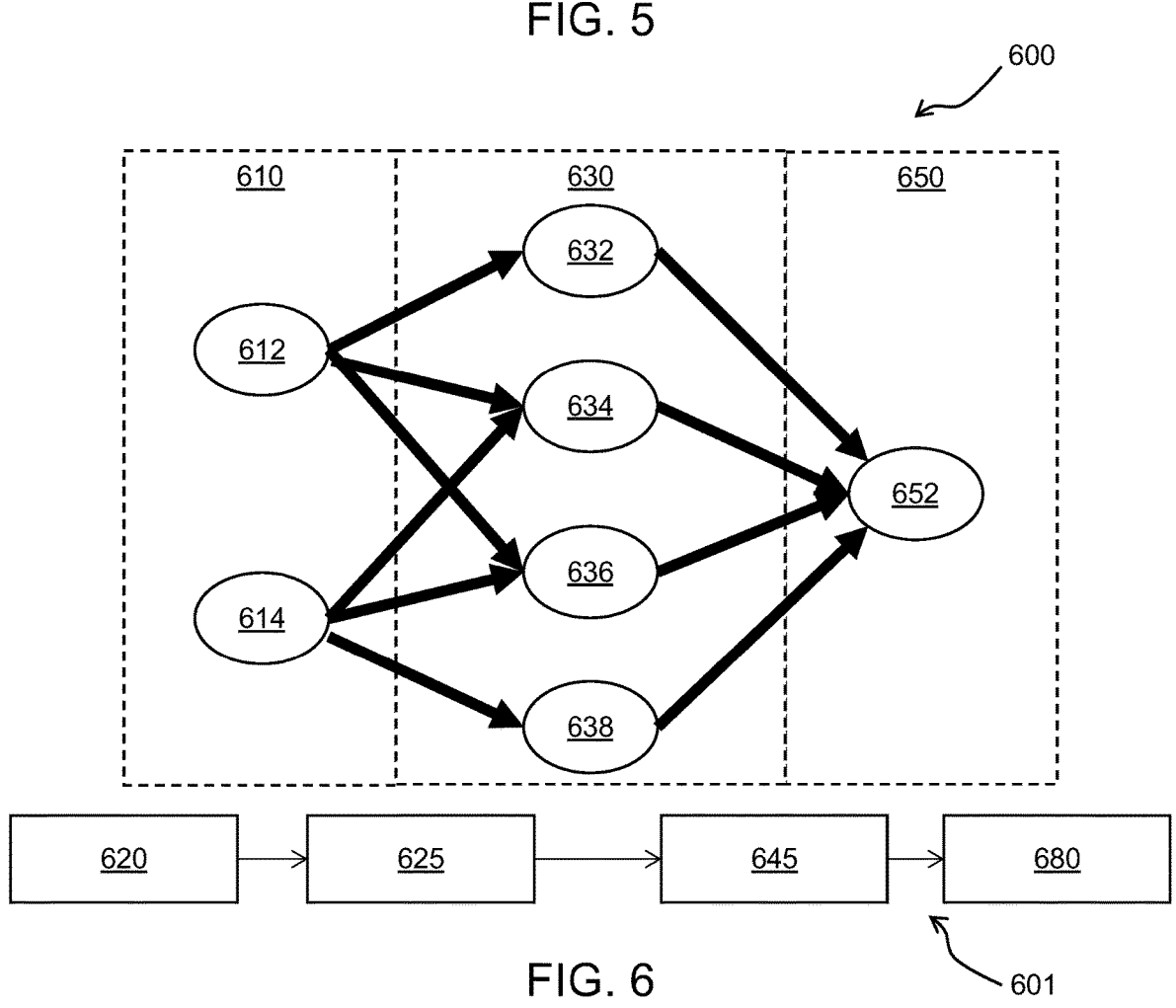
FIG. 6 illustrates an example of a neural network and a method performed in the neural network according to one or more embodiments.

FIG. 6 illustrates an example of a neural network 600 and a method 601 performed in the neural network 600 according to one or more embodiments. The description of FIG. 6 is made with reference to FIGS. 1-5 for ease of understanding where appropriate.

The neural network 600 operates to support implementation of the ML/AI algorithms (e.g., as implemented by the determination engine 101 of FIGS. 1-2) described herein. The neural network 600 can be implemented in hardware, such as the machine 520 and/or the hardware 550 of FIG. 5.

In an example operation, the determination engine 101 includes collecting the data 510 from the hardware 550. In the neural network 600, an input layer 610 is represented by a plurality of inputs (e.g., inputs 612 and 614 of FIG. 6). With respect to block 620 of the method 601, the input layer 610 receives the inputs 612 and 614. The inputs 612 and 614 can include a dataset with one or more predictors. For example, the collecting of the data 510 can be an aggregation of health record information 312 from the first source 310 and the diagnostic measurements 322 from the second source 320 into a dataset.

At block 625 of the method 601, the neural network 600 encodes the inputs 612 and 614 utilizing any portion of the data 510 (e.g., the dataset and predictions produced by the artificial intelligence diagram 500) to produce a latent representation or data coding. The latent representation includes one or more intermediary data representations derived from the plurality of inputs. According to one or more embodiments, the latent representation is generated by an element-wise activation function (e.g., a sigmoid function or a rectified linear unit) of the determination engine 101. As shown in FIG. 6, the inputs 612 and 614 are provided to a hidden layer 630 depicted as including nodes 632, 634, 636, and 638. The neural network 600 performs the processing via the hidden layer 630 of the nodes 632, 634, 636, and 638 to exhibit complex global behavior, determined by the connections between the processing elements and element parameters. Thus, the transition between layers 610 and 630 can be considered an encoder stage that takes the inputs 612 and 614 and transfers it to a deep neural network (within layer 630) to learn some smaller representation of the input (e.g., a resulting the latent representation).

The deep neural network can be a CNN, a long short-term memory neural network, a fully connected neural network, or combination thereof. This encoding provides a dimensionality reduction of the inputs 612 and 614 (in some cases, encoding aligns with operations of the simplification model). Dimensionality reduction is a process of reducing the number of random variables (of the inputs 612 and 614) under consideration by obtaining a set of principal variables. For instance, dimensionality reduction can be a feature extraction that transforms data (e.g., the inputs 612 and 614) from a high-dimensional space (e.g., more than 10 dimensions) to a lower-dimensional space (e.g., 2-3 dimensions). The technical effects and benefits of dimensionality reduction include reducing time and storage space requirements for the data 510, improving visualization of the data 510, and improving parameter interpretation for machine learning. In the case of implementing the simplification model the model 530, the parameter interpretation can improve as the model 530 moves from the SM to the linear regression and also into white-boxing to stabilize, learn, and identify parameters. This data transformation can be linear or nonlinear. The operations of receiving (block 620) and encoding (block 625) can be considered a data preparation portion (e.g., where parameter interpretation is implemented by the simplification model and/or white-boxing) of the multi-step data manipulation by the determination engine 101.

At block 645 of the method 601, the neural network 600 decodes the latent representation. The decoding stage takes the encoder output (e.g., the resulting the latent representation) and attempts to reconstruct some form of the inputs 612 and 614 using another deep neural network. In this regard, the nodes 632, 634, 636, and 638 are combined to produce in an output layer 650 an output 652, as shown in block 680 of the method 601. That is, the output layer 650 reconstructs the inputs 612 and 614 on a reduced dimension but without the signal interferences, signal artifacts, and signal noise.

Figure 7:
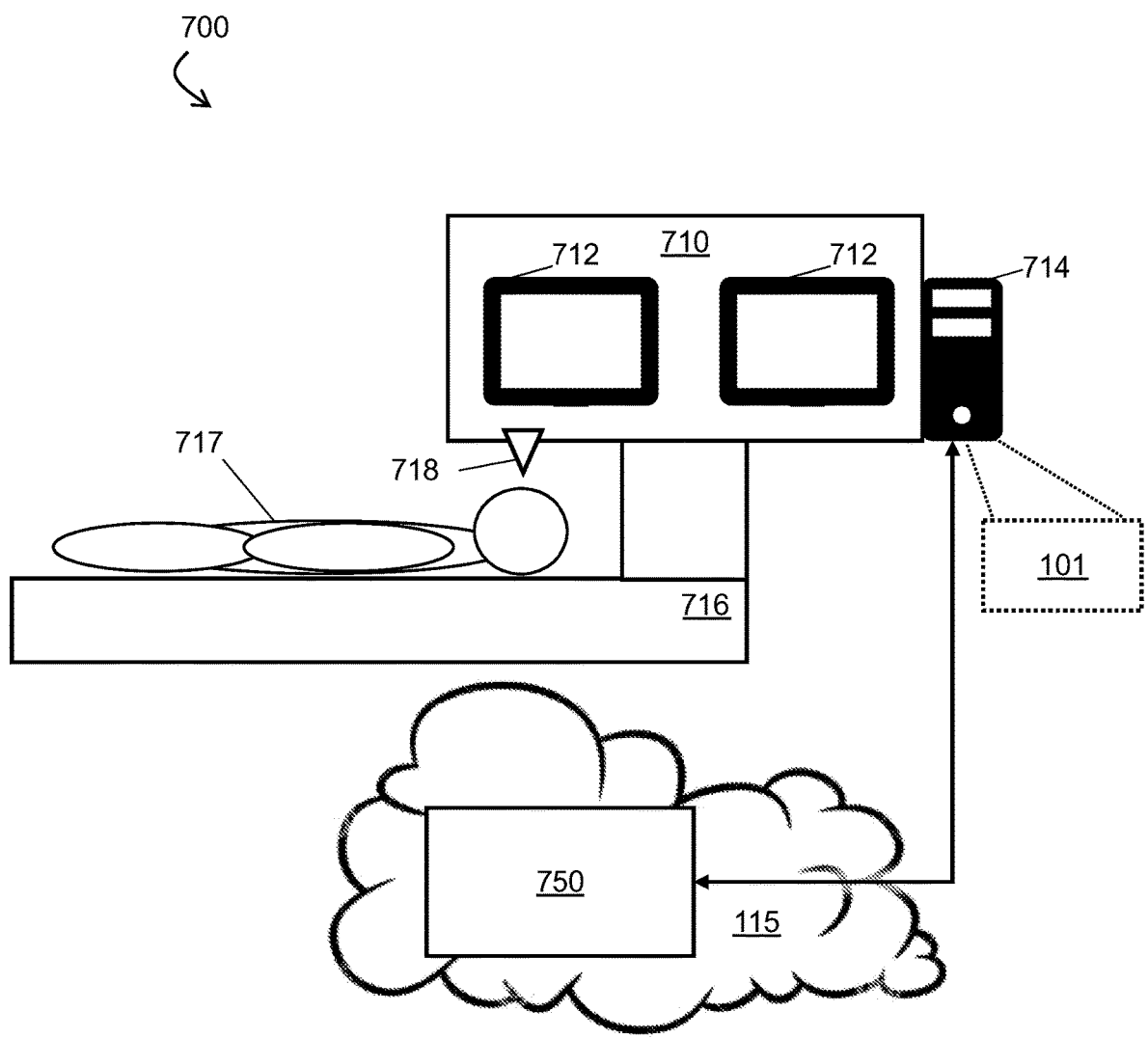
FIG. 7 illustrates a system according to one or more embodiments.

FIG. 7 is a system 700 according to one or more embodiments. Note that items and elements of the system 700, while shown in the singular, are representative of one or more of that item or element. The system 100 illustrates a determination engine 101 stored and operating within hardware and software of a laser apparatus 710 to predict post-operative manifest refraction and to account for post-operative lens settlement by selecting IOLs with corresponding lens power or other parameters such that after settlement, they will provide zero or near-zero manifest refraction. The laser apparatus 710 can be an infrared laser. For example, the system 700 can be the CATALYS™ Precision Laser System, which includes (OCT), and utilizes a femtosecond laser as the laser apparatus 710. The laser apparatus 710 can include one or more displays 712 (that present user interfaces) as well as a computing sub-system 714 (i.e. a computer with a processor 141 and a memory 132) which stores and operates the determination engine 101. The laser apparatus 710 can include a table 716 for supporting a patient 717. The laser apparatus 710 can include a laser 718 that performs medical procedures, scanning, etc. on the patient 717. The laser apparatus 710 can communicate with the cloud environment 115 or similar network to access computing environments 750 (e.g., data/web services 120, clinical data, calculators, etc.).

Operations of the system 700 can include the methods and processes discussed herein. By way of example, the system 700 implements the determination engine 330 to at least infer interoperative data, infer an ideal manifest refraction spherical equivalent or spherical and cylindrical power to reach a zero or near zero refraction for the patient 717, seek and determine the best predictors that infer/predicts a final surgical outcome for a patient 717, and selects or suggests an IOL implant. Further, the displays 712 can present user interface to enable interactions with and viewing of the operations of the determination engine 101, such as seeing an IOL selection by the determination engine 101. By way of example, the medical professional 150 can interact with the determination engine 101, via the application 145, to set medical goals in the system 700. These medical goals contribute to the IOL selection. Thus, if the system 700 is presenting on the displays 712 predicted post-operative manifest refraction, the medial professional 150 may select a corresponding new lens that will achieve a zero or near zero post-operative manifest refraction error for the patient 717, (e.g. changing the medical goal to −1 (instead of zero) and selecting another IOL).

According to an embodiment, a method is provided. The method includes generating, by a determination engine executed by one or more processors, a predictive feature set of one or more predictors associated with diagnostic measurements of one or more eyes. The method also includes performing, by the determination engine, a recursive selection operation using one or more combinations within the predictive feature set and one or more models to produce a most predictive subset, the most predictive subset having a highest prediction accuracy among other predictive subsets for post-operative manifest refraction for training data comprising diagnostic measurements and measured post-operative outcomes being associated with one or more optimal attributes of the diagnostic measurements that provide a prediction with zero or near zero post-operative manifest refraction error. The method also includes generating, by the determination engine, a determination model by refining and retraining the one or more models of the recursive selection operation utilizing the most predictive subset, the determination model accounting for post-operative lens settlement.

In some embodiments, the diagnostic measurements comprise dry data from one or more diagnostic machines, the dry data comprising at least structural anatomy of the one or more eyes or position of an original crystalline lens. In some embodiments, the diagnostic measurements accounts for the post-operative lens settlement absent post-operative lens position calculations. In some embodiments, post-operative lens settlement comprises lateral and axial movement in a z-direction. In some embodiments, the recursive selection operation comprises a recursive linear elimination process. In a further embodiment, the recursive linear elimination process may be performed on a basis of a linear support-vector machine. In some embodiments, the determination model comprises a support-vector machine comprising a radial basis function. In some embodiments, the one or more models comprise a support-vector machine and a linear regression algorithm. In some embodiments, the most predictive subset of the one or more predictors are inputs to the determination model and a remaining set of the one or more predictors are not utilized by the determination model. In some embodiments, a number of the one or more predictors is equal to or greater than 1000, and a number of the most predictive subset of the one or more predictors is equal to or less than 50. In some embodiments, the most predictive subset of the one or more predictors are recursively selected with respect to rates of success and accuracy rankings. In a further embodiment, the determination engine comprises at least one of a mean absolute error, median absolute error, root means square error algorithm, and proportion of eyes within a diopter range to determine the rates of success and accuracy rankings for the one or more predictors.

In some embodiments, the determination engine acquires a dataset comprising the diagnostic measurements corresponding to a plurality of patients, the diagnostic measurements comprising at least one selected lens attribute for each of the plurality of patients. In a further embodiment, the at least one selected lens attribute comprises a lens type or a lens power. In another further embodiment, the dataset comprises health record information from a first source and the diagnostic measurements are acquired from a second source. In a still further embodiment, the dataset comprises doctor diagnosis information across the health record information and the diagnostic measurements.

In some embodiments, the diagnostic measurements comprise pre-operative intraocular lens measurement data, such as measurement data from an optical biometer system; precision measurement data; three dimensional data; and biometry data derived from the three dimensional data. Multiple devices are available on the market to take the pre-operative intraocular lens measurements. Examples of two such devices are the IOL Master system, manufactured by Carl Zeiss AG of Oberkochen, Germany, and the Lenstar LS 900 from Haag-Streit USA, Inc. of Mason, Ohio. In a further embodiment, the precision measurement data comprises pre-lens placement information related to final patient vision comprising the zero or near zero post-operative manifest refraction.

In some embodiments, the near zero post-operative manifest refraction includes a tolerance of about +/−0.5 diopters from 0. In a further embodiment, the near zero post-operative manifest refraction is skewed around a negative half of the tolerance. In some embodiments, the determination model utilizes pre-operative data as an input according to the most predictive subset. In some embodiments, the determination model utilizes one or more outputs of one or more algorithms that use the pre-operative data as the input according to the most predictive subset. In some embodiments, the most predictive subset has a prediction accuracy based on a difference between predicted spherical equivalence and actual spherical equivalence that resulted in zero or near zero. In some embodiments, the most predictive subset has a prediction accuracy within about 0.5 D, about 0.75 D, or about 1.0 D of an absolute error. In some embodiments, the determination engine sets minimum thresholds for prediction accuracy. In some embodiments, generating the predictive feature set comprises generating a plurality of predictive subsets comprising different combinations of predictors. In some embodiments, refining the one or more models of the recursive selection operation comprises performing a linear regression algorithm on a plurality of predictors of the most predictive subset. In some embodiments, the determination model accounts for post-operative outcomes for one or more of a monofocal lens, a multifocal lens, a toric lens, an extended depth-of-focus lens, an adjustable lens, or an accommodative lens.

According to another embodiment, a method is provided. The method includes receiving, by a determination engine executed by one or more processors, a first set of diagnostic measurements of one or more eyes prior to undergoing intraocular lens (IOL) implantation. The method also includes calculating, by the determination engine using the first set of diagnostic measurements, an intermediate prediction of post-operative manifest refraction that accounts for post-operative lens settlement. The method also includes receiving, by the determination engine, a plurality of cornea apex position and curvature measurements of the one or more eyes. The method also includes generating, by the determination engine, a predictive feature subset comprising one or more of the plurality of cornea apex position and curvature measurements, the first set of diagnostic measurements, and the intermediate prediction. The method also includes calculating, by the determination engine using the predictive feature subset, a final prediction of post-operative manifest refraction that accounts for post-operative lens settlement associated with one or more IOL parameters, wherein an IOL associated with the one or more IOL parameters is selected for implantation responsive to the final prediction of post-operative manifest refraction being below a threshold.

In some embodiments, calculating the final prediction comprises performing a linear regression algorithm on the predictive feature subset. In a further embodiment, the predictive feature subset comprises a subset of the one or more of the plurality of cornea apex position and curvature measurements, the first set of diagnostic measurements, and the intermediate prediction having a highest prediction accuracy among other subsets for post-operative manifest refraction that accounts for post-operative lens settlement for training data comprising diagnostic measurements and measured post-operative lens settlement outcomes.

According to one or more embodiments, any of the method embodiments above can be implemented as an apparatus, a system, and/or a computer program product.

According to another embodiment, a system is provided. The system comprises an infrared laser, and a computing sub-system comprising a memory storing a determination engine and a processor executing the determination engine. In embodiments, the determination engine during execution is configured to: receive a first set of diagnostic measurements of one or more eyes prior to undergoing intraocular lens (IOL) implantation; calculate, using the first set of diagnostic measurements, an intermediate prediction of post-operative manifest refraction; receive, via the infrared laser, a plurality of cornea apex position and curvature measurements of the one or more eyes; generate a predictive feature subset comprising one or more of the plurality of cornea apex position and curvature measurements, the first set of diagnostic measurements, and the intermediate prediction; and calculate, using the predictive feature subset, a final prediction of post-operative manifest refraction associated with one or more IOL parameters, wherein an IOL associated with the one or more IOL parameters is selected for implantation responsive to the final prediction of post-operative manifest refraction being zero or near zero.

According to another embodiment, a laser apparatus is provided. The laser apparatus includes an infrared laser; and a computing sub-system comprising a memory storing a determination engine and a processor executing the determination engine. In embodiments, the determination engine during execution is configured to cause the laser apparatus to: generate a predictive feature set of one or more predictors associated with diagnostic measurements of one or more eyes; perform a recursive selection operation using one or more combinations within the predictive feature set and one or more models to produce a most predictive subset, the most predictive subset having a highest prediction accuracy among other predictive subsets for zero or near zero post-operative manifest refraction for training data comprising diagnostic measurements and measured post-operative outcomes; and generate a determination model by refining and retraining the one or more models of the recursive selection operation utilizing the most predictive subset.

According to one or more embodiments, the laser apparatus embodiment above can be implemented as a method, a system, and/or a computer program product.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

The intraocular lenses discussed herein may be of any type and form, including monofocal lenses, toric lenses, multifocal lenses (e.g. including bifocal lenses, trifocal lenses, or any other number of focal points, including multifocal toric lenses), extended depth-of-focus lenses, adjustable lenses, accommodative lenses, or any other type of IOL. Lenses may be of any suitable material, including silicone, polymethylmethacrylate, acrylic, or any combination of these or other materials, and may be clear, tinted, UV filtering, polarized, or have any other suitable characteristics.

As discussed above, the aforementioned systems and methods may be used to predict the optical power most likely to result in zero or near zero post-operative manifest refraction error for a patient. This statement is true for all types of lenses including, but not limited to, monofocal lenses, toric lenses, monofocal torical lenses, multifocal lenses, extended depth-of-focus lenses, adjustable lenses, accommodative lenses, or any other type of IOL.

In one embodiment of the present disclosure, the systems and methods discussed herein are used to predict the desired power for a monofocal intraocular lens for a patient.

As one of reasonable skill in the art will recognize, the systems and methods discussed herein are used to predict cylinder power for a patient with astigmatism.

In one embodiment of the present disclosure, the systems and methods discussed herein are used to predict the desired add power for a bifocal or multifocal intraocular lens for a patient.

In one embodiment of the present disclosure, the systems and methods discussed herein are used to predict the desired add power for an extended depth-of-focus (EDOF) intraocular lens for a patient.

Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
   receiving, by a determination engine executed by one or more processors, a first set of diagnostic measurements of one or more eyes prior to undergoing intraocular lens (IOL) implantation;
   calculating, by the determination engine using the first set of diagnostic measurements, an intermediate prediction of post-operative manifest refraction;
   receiving, by the determination engine, a plurality of cornea apex position and curvature measurements of the one or more eyes;
   generating, by the determination engine, a predictive feature subset comprising one or more of the plurality of cornea apex position and curvature measurements, the first set of diagnostic measurements, and the intermediate prediction;
   calculating, by the determination engine using the predictive feature subset, a final prediction of post-operative manifest refraction associated with one or more IOL parameters, wherein an IOL associated with the one or more IOL parameters is selected for implantation responsive to the final prediction of post-operative manifest refraction being zero or near zero.

2. The method of claim 1, wherein calculating the final prediction comprises performing a linear regression algorithm on the predictive feature subset.

3. The method of claim 2, wherein the predictive feature subset comprises a subset of the one or more of the plurality of cornea apex position and curvature measurements, the first set of diagnostic measurements, and the intermediate prediction having a highest prediction accuracy among other subsets for post-operative manifest refraction for training data comprising diagnostic measurements and measured post-operative outcomes.

4. The method of claim 1, wherein the IOL is selected from a monofocal IOL, a multifocal IOL, a toric IOL, an extended depth-of-focus IOL, an adjustable IOL, or an accommodative IOL.

5. A system, comprising:
   an infrared laser; and
   a computing sub-system comprising a memory storing a determination engine and a processor executing the determination engine, wherein the determination engine during execution is configured to:
   receive a first set of diagnostic measurements of one or more eyes prior to undergoing intraocular lens (IOL) implantation,
   calculate, using the first set of diagnostic measurements, an intermediate prediction of post-operative manifest refraction,
   receive, via the infrared laser, a plurality of cornea apex position and curvature measurements of the one or more eyes,
   generate a predictive feature subset comprising one or more of the plurality of cornea apex position and curvature measurements, the first set of diagnostic measurements, and the intermediate prediction, and
   calculate, using the predictive feature subset, a final prediction of post-operative manifest refraction associated with one or more IOL parameters, wherein an IOL associated with the one or more IOL parameters is selected for implantation responsive to the final prediction of post-operative manifest refraction being zero or near zero.

6. The system of claim 5, wherein the IOL is selected from a monofocal IOL, a multifocal IOL, a toric IOL, an extended depth-of-focus IOL, an adjustable IOL, or an accommodative IOL.

* * * * *